United States Patent
Nakamura et al.

(10) Patent No.: US 9,284,324 B2
(45) Date of Patent: Mar. 15, 2016

(54) PHENYLPYRROLE DERIVATIVE

(71) Applicant: TAISHO PHARMACEUTICAL CO., LTD, Toshima-ku, Tokyo (JP)

(72) Inventors: Toshio Nakamura, Toshima-ku (JP); Seiji Masuda, Toshima-ku (JP)

(73) Assignee: TAISHO PHARMACEUTICAL CO., LTD, Tokyo (JP)

(*) Notice: Subject to any disclaimer, the term of this patent is extended or adjusted under 35 U.S.C. 154(b) by 0 days.

(21) Appl. No.: 14/362,939

(22) PCT Filed: Dec. 7, 2012

(86) PCT No.: PCT/JP2012/081744
§ 371 (c)(1),
(2) Date: Jun. 5, 2014

(87) PCT Pub. No.: WO2013/085018
PCT Pub. Date: Jun. 13, 2013

(65) Prior Publication Data
US 2014/0330010 A1 Nov. 6, 2014

(30) Foreign Application Priority Data

Dec. 8, 2011 (JP) ................... 2011-268561

(51) Int. Cl.
| | | |
|---|---|---|
| C07D 295/00 | (2006.01) | |
| C07D 491/107 | (2006.01) | |
| C07D 413/14 | (2006.01) | |
| A61K 31/4025 | (2006.01) | |
| A61K 31/454 | (2006.01) | |
| A61K 31/5377 | (2006.01) | |
| C07D 401/12 | (2006.01) | |
| C07D 403/12 | (2006.01) | |

(52) U.S. Cl.
CPC ........ *C07D 491/107* (2013.01); *A61K 31/4025* (2013.01); *A61K 31/454* (2013.01); *A61K 31/5377* (2013.01); *C07D 401/12* (2013.01); *C07D 403/12* (2013.01); *C07D 413/14* (2013.01)

(58) Field of Classification Search
CPC .................................................. C07D 401/12
USPC .......................................................... 548/531
See application file for complete search history.

(56) References Cited

U.S. PATENT DOCUMENTS

| | | | |
|---|---|---|---|
| 2007/0105834 A1 | 5/2007 | Diaz-Martin et al. | |
| 2010/0113776 A1* | 5/2010 | Nakamura | C07D 401/12 544/130 |
| 2010/0267687 A1 | 10/2010 | Nakamura et al. | |
| 2011/0065668 A1 | 3/2011 | Nakamura et al. | |

FOREIGN PATENT DOCUMENTS

| | | |
|---|---|---|
| JP | 2010285423 | 12/2010 |
| WO | 0212190 | 2/2002 |

(Continued)

OTHER PUBLICATIONS

Faghih et al., "Aminoalkoxybiphenylnitriles as histamine-3 receptor ligands" Bioorganic & Medicinal Chemistry Letters, 12:3077-3079 (2002).

(Continued)

*Primary Examiner* — Nizal Chandrakumar
(74) *Attorney, Agent, or Firm* — Sughrue Mion, PLLC

(57) ABSTRACT

Provided are novel compounds that are useful in the prevention or treatment of such diseases as dementia, Alzheimer's disease, attention-deficient hyperactivity disorder, schizophrenia, epilepsy, central convulsion, obesity, diabetes mellitus, hyperlipidemia, narcolepsy, idiopathic hypersomnia, behaviorally induced insufficient sleep syndrome, sleep apnea syndrome, circadian rhythm disorder, parasomnia, sleep related movement disorder, insomnia, and depression, or allergic rhinitis, or pharmaceutically acceptable salts of such compounds. Specifically, there are provided phenylpyrrole compounds represented by the following formula (I) or pharmaceutically acceptable salts thereof:

Formula (I)

[Chemical formula 1]

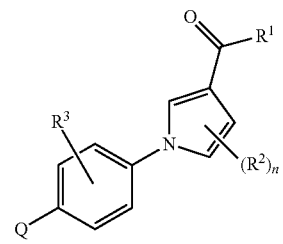

(I)

[wherein Q refers to a group represented by the following formula (A) or (B):

[Chemical formula 2]

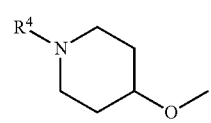

(A)

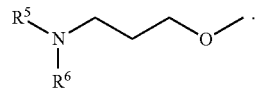

(B)

8 Claims, No Drawings

(56) References Cited

FOREIGN PATENT DOCUMENTS

| | | |
|---|---|---|
| WO | 2005089747 | 9/2005 |
| WO | 2005097751 | 10/2005 |
| WO | 2005097778 | 10/2005 |
| WO | 2005118547 | 12/2005 |
| WO | 2006014136 | 2/2006 |
| WO | 2006045416 | 5/2006 |
| WO | 2006046131 | 5/2006 |
| WO | 2006059778 | 6/2006 |
| WO | 2006061193 | 6/2006 |
| WO | 2006103045 | 10/2006 |
| WO | 2006103057 | 10/2006 |
| WO | 2006107661 | 10/2006 |
| WO | 2006117609 | 11/2006 |
| WO | 2007094962 | 8/2007 |
| WO | 2008072703 | 6/2008 |
| WO | 2008072724 | 6/2008 |
| WO | 2009063953 | 5/2009 |

OTHER PUBLICATIONS

International Preliminary Report on Patentability for PCT/JP2012/081744 dated Jun. 10, 2014, with Written Opinion (dated Jan. 22, 2013).

Communication dated Jun. 1, 2015 from the European Patent Office in counterpart European Application No. 12855074.6.

Written Opinion for Singapore Application No. 11201402963T dated Mar. 2, 2015.

Communication for European Application No. 12861932.7 dated Jun. 2, 2015 (along with Supplementary European Search Report (dated May 23, 2015)).

* cited by examiner

PHENYLPYRROLE DERIVATIVE

CROSS REFERENCE TO RELATED APPLICATIONS

This application is a National Stage of International Application No. PCT/JP2012/081744 filed Dec. 7, 2012, claiming priority based on Japanese Patent Application No. 2011-268561 filed Dec. 8, 2011, the contents of all of which are incorporated herein by reference in their entirety.

TECHNICAL FIELD

The present invention relates to novel phenylpyrrole derivatives and pharmaceutical uses thereof, in particular, preventive or therapeutic agents for diseases associated with histamine H3 receptors.

BACKGROUND ART

Histamine is normally stored within intracellular granules in mast cells, lung, liver and gastric mucosa, etc. and released from the cell in response to external stimuli such as antigen-binding to an antibody on the cell surface. For example, when mast cells are stimulated by an antigen entering from outside, histamine is released from the mast cells and stimulates histamine H1 (H1) receptors located on blood vessels or smooth muscles, thereby triggering an allergic reaction. Likewise, histamine released from ELC cells (enterochromaffin-like cells) on the gastric mucosa stimulates histamine H2 (H2) receptors on the parietal cells to promote gastric acid secretion. Based on these facts, H1 and H2 receptor antagonists have been developed as therapeutic agents for allergic diseases and gastric ulcer, respectively, and currently find wide use as medicaments.

It has been found that histamine serves as a neurotransmitter and acts on histamine receptors (histamine H3 (H3) receptors) located on the central and peripheral nerves to exhibit various physiological functions. This receptor was cloned in 1999, and its gene sequence and amino acid sequence were determined. However, the amino acid sequence of H3 receptor has only 22% and 21.4% homology with those of H1 receptor and H2 receptor, respectively (see Non-Patent Document 1). H3 receptors which are present in the presynaptic membrane have been shown to serve as autoreceptors that control the synthesis and release of histamine (see Non-Patent Document 2). In addition to that, H3 receptors have been shown to control the release of other neurotransmitters including acetylcholine, serotonin, dopamine, and noradrenaline (see Non-Patent Document 3). It has also been suggested that H3 receptors are active in the absence of agonists and this activity is able to be inhibited by compounds acting as inverse agonists. These facts suggest that H3 receptor antagonists or inverse agonists enhance the release of H3 receptor-controlled neurotransmitters and may potentially serve as therapeutic agents for various diseases associated with abnormal release thereof.

As a matter of fact, results of experiments with animal models show the possibility that H3 receptor antagonists or inverse agonists can be used as therapeutic agents for dementia, Alzheimer's disease (see Non-Patent Documents 4 and 5), attention-deficit hyperactivity disorder (see Non-Patent Document 6), schizophrenia (see Non-Patent Document 7), epilepsy, central convulsion, etc.

It has been shown that H3 receptors are involved in the eating behavior (see Non-Patent Document 8) and metabolic diseases including obesity, diabetes mellitus, hyperlipidemia, etc. are also assumed as diseases for which H3 receptor antagonists or inverse agonists are indicated.

It has been shown that histamine regulates the circadian rhythm in the brain and is responsible for maintaining the balance between waking and sleeping states (see Non-Patent Documents 9 and 10) and diseases associated with sleep disorders, including narcolepsy, idiopathic hypersomnia, behaviorally induced insufficient sleep syndrome, sleep apnea syndrome, circadian rhythm disorder, parasomnia, sleep related movement disorder, insomnia, and depression, are also assumed as diseases for which H3 receptor antagonists or inverse agonists are indicated.

It has been shown that H3 receptors are present in sympathetic nerves on the nasal mucosa, and reported that the combined use of H3 and H1 receptor antagonists improved nasal congestion significantly (see Non-Patent Document 11). This indicates the possibility that H3 receptor antagonists or inverse agonists are useful for treatment of such diseases as allergic rhinitis when they are used either alone or in combination with H1 receptor antagonists.

Outlines of H3 receptor antagonists or inverse agonists are found in several reviews (see Non-Patent Documents 12 to 15) to which reference may be had. In earlier years, there have been reported many imidazole compounds which were derived from histamine itself as a lead compound. However, those have yet to be developed as medicaments due to the concerns of the inhibition of the drug-metabolizing enzyme cytochrome P450 (CYP).

In recent years, non-imidazole H3 receptor antagonists or inverse agonists have been reported in many documents and patents (see Patent Documents 1 to 10).

Reports have also been made of histamine H3 receptor antagonists having 5-membered aromatic rings such as the pyrazole ring (see Patent Documents 11 to 14). In addition, there has been reported a histamine H3 receptor antagonist having an aryloxypiperidine skeleton that is substituted by an unsubstituted pyrrole (see Patent Document 15). However, there has been no report about compounds having the structures disclosed hereinafter.

CITATION LIST

Patent Documents

Patent Document 1: International Patent Publication WO2005097751
Patent Document 2: International Patent Publication WO2005097778
Patent Document 3: International Patent Publication WO2005118547
Patent Document 4: International Patent Publication WO2006014136
Patent Document 5: International Patent Publication WO2006045416
Patent Document 6: International Patent Publication WO2006046131
Patent Document 7: International Patent Publication WO2006059778
Patent Document 8: International Patent Publication WO2006061193
Patent Document 9: International Patent Publication WO2006107661
Patent Document 10: International Patent Publication WO2006103057
Patent Document 11: International Patent Publication WO2006103045

Patent Document 12: International Patent Publication WO2007094962
Patent Document 13: International Patent Publication WO2008072724
Patent Document 14: International Patent Publication WO2009063953
Patent Document 15: International Patent Publication WO2002012190

Non-Patent Documents

Non-Patent Document 1: Lovenberg T. W. et al., Molecular pharmacology, 55, 1101-1107, 1999
Non-Patent Document 2: Arrang J-M. et al., Nature, 302, 832-837, 1983
Non-Patent Document 3: Brown R. E. et al., Progress in Neurobiology, 63, 637-672, 2001
Non-Patent Document 4: Huang Y-W. et al., Behavioural Brain Research, 151, 287-293, 2004
Non-Patent Document 5: Komater V. A. et al., Behavioural Brain Research, 159, 295-300, 2005
Non-Patent Document 6: Passani M. B. et al., Neuroscience and Biobehavioral Reviews, 24, 107-113, 2000
Non-Patent Document 7: Fox G. B. et al., J. Pharmacol. Exp. Ther., 313, 176-190, 2005
Non-Patent Document 8: Hancock A. A. et al., Curr. Opin. Investig. Drug, 4, 1190-1197
Non-Patent Document 9: Huang Z-L. et al., Prog. Natr. Acad. Sci., 103, 4687-4692, 2006
Non-Patent Document 10: Babier A. J. et al., Br. J. Pharmacol., 143, 649-661, 2004
Non-Patent Document 11: McLeod R. L. et al., Am. J. Rhinol., 13, 391-399, 1999
Non-Patent Document 12: Schwartz J. C. et al., Trends in Pharmacol. Sci., 7, 24-28, 1986
Non-Patent Document 13: Passani M. B. et al., Trends in Pharmacol. Sci., 25, 618-625, 2004
Non-Patent Document 14: Leurs R. et al., Nature Drug Discovery, 4, 107-122, 2005
Non-Patent Document 15: Leurs R. et al., Drug Discovery Today, 10, 1613-1627, 2005

SUMMARY OF THE INVENTION

Technical Problem

The present invention has as an object providing novel compounds or their pharmaceutically acceptable salts, which have a potent action for inhibiting the binding of histamine to the histamine H3 receptor and which are useful in the prevention or treatment of disorders due to the histamine H3 receptor, for example, such diseases as dementia, Alzheimer's disease, attention-deficient hyperactivity disorder, schizophrenia, epilepsy, central convulsion, obesity, diabetes mellitus, hyperlipidemia, narcolepsy, idiopathic hypersomnia, behaviorally induced insufficient sleep syndrome, sleep apnea syndrome, circadian rhythm disorder, parasomnia, sleep related movement disorder, insomnia, and depression, or allergic rhinitis.

Solution to Problem

To attain the above-stated object, the present inventors conducted intensive studies and found as a result that phenylpyrrole derivatives having a carbonyl substituent at 3-position of the pyrrole ring exhibited potent inhibitory activity against the binding of histamine to the histamine H3 receptor. This finding has led to the completion of the present invention.

Hereinafter, the present invention will be described in detail. Embodiments of the present invention (compound embodiments will be called "the inventive compounds") are as shown below.

Briefly, the present invention relates to:

(1) A compound represented by formula (I)

[Chemical formula 1]

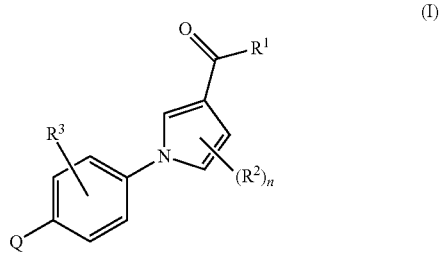

[wherein
Q refers to a group represented by the following formula (A) or (B):

[Chemical formula 2]

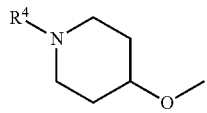

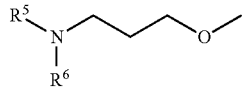

$R^1$ is hydroxyl, $C_1$-$C_6$ alkoxy, or $NR^{1A}R^{1B}$;
$R^{1A}$ and $R^{1B}$, which may be the same or different, are each a hydrogen atom, $C_1$-$C_6$ alkyl or $C_3$-$C_7$ cycloalkyl, or
$R^{1A}$ and $R^{1B}$ are bonded together with the adjacent nitrogen atom to form a 3- to 7-membered saturated heterocyclic ring (the saturated heterocyclic ring being optionally substituted by one or two $C_1$-$C_6$ alkyls);
$R^2$ is a hydrogen atom, a halogen atom, or $C_1$-$C_6$ alkyl;
n is 1 or 2;
$R^3$ is a hydrogen atom, a halogen atom, or $C_1$-$C_6$ alkyl;
$R^4$ is $C_1$-$C_6$ alkyl (the $C_1$-$C_6$ alkyl may be substituted by one or two $C_3$-$C_7$ cycloalkyls) or $C_3$-$C_7$ cycloalkyl (the $C_3$-$C_7$ cycloalkyl may be substituted by one or two $C_1$-$C_6$ alkyls);
$R^5$ and $R^6$, which may be the same or different, are each $C_1$-$C_6$ alkyl or $C_3$-$C_7$ cycloalkyl, or $R^5$ and $R^6$ are bonded together with the adjacent nitrogen atom to form a 3- to 7-membered saturated heterocyclic ring (the saturated heterocyclic ring being optionally substituted by one or two $C_1$-$C_6$ alkyls)] or a pharmaceutically acceptable salt thereof.

(2) A compound as recited in (1), wherein Q is represented by formula (A):

[Chemical formula 3]

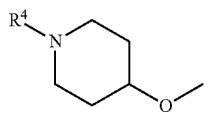

(A)

(wherein $R^4$ is as defined in (1)) or a pharmaceutically acceptable salt thereof.

(3) A compound as recited in (1) or (2), wherein $R^1$ is $NR^{1A}R^{1B}$ (wherein $R^{1A}$ and $R^{1B}$ are as defined in (1)) or a pharmaceutically acceptable salt thereof.

(4) A compound as recited in any one of (1) to (3), wherein $R^2$ and $R^3$ are each a hydrogen atom and n is 1, or a pharmaceutically acceptable salt thereof.

(5) A compound as recited in any one of (1) to (4), wherein $R^4$ is $C_3$-$C_7$ cycloalkyl or a pharmaceutically acceptable salt thereof.

(6) A pharmaceutical agent comprising as the active ingredient a compound as recited in any one of (1) to (5) or a pharmaceutically acceptable salt thereof.

(7) A pharmaceutical agent as recited in (6) which is a histamine H3 receptor antagonist or inverse agonist.

(8) A pharmaceutical agent as recited in (6) or (7) which is a preventive or therapeutic agent for dementia, Alzheimer's disease, attention-deficient hyperactivity disorder, schizophrenia, epilepsy, central convulsion, obesity, diabetes mellitus, hyperlipidemia, narcolepsy, idiopathic hypersomnia, behaviorally induced insufficient sleep syndrome, sleep apnea syndrome, circadian rhythm disorder, parasomnia, sleep related movement disorder, insomnia, depression, or allergic rhinitis.

Advantageous Effects of the Invention

The compounds of the present invention have an outstanding histamine H3 receptor antagonistic action.

DESCRIPTION OF EMBODIMENTS

The terms and expressions used herein are as defined below.

The "halogen atom" as used herein refers to a fluorine atom, a chlorine atom, a bromine atom, or an iodine atom.

The "$C_1$-$C_6$ alkyl" as used herein refers to a linear or branched alkyl group having 1 to 6 carbon atoms and may be exemplified by such groups as methyl, ethyl, n-propyl, isopropyl, n-butyl, isobutyl, sec-butyl, tert-butyl, n-pentyl, isopentyl, neopentyl, or n-hexyl.

The "$C_3$-$C_7$ cycloalkyl" as used herein refers to a cyclopropyl, cyclobutyl, cyclopentyl, cyclohexyl or cycloheptyl group.

The "$C_1$-$C_6$ alkoxy" as used herein refers to a linear or branched alkoxy group having 1 to 6 carbon atoms and may be exemplified by such groups as methoxy, ethoxy, n-propoxy, isopropoxy, n-butoxy, isobutoxy, sec-butoxy, tert-butoxy, n-pentyloxy, isopentyloxy, neopentyloxy, or n-hexyloxy.

The "3- to 7-membered saturated heterocyclic ring" in the expression "bonded together with the adjacent nitrogen atom to form a 3- to 7-membered saturated heterocyclic ring" refers to a saturated monocyclic ring or spiroling that is composed of 3 to 7 ring forming atoms and which contains said adjacent nitrogen atom, with optional additional inclusion of a single hetero atom selected from among O, N, and S; examples may include such groups as 1-aziridinyl, 1-azetidinyl, 1-pyrrolidinyl, piperidino, 1-azepanyl, morpholino, or 2-oxa-6-azaspiro[3,3]heptan-6-yl.

Preferred embodiments of the inventive compounds are shown below.

One preferred embodiment of the compound of formula (I) according to the present invention is where Q is represented by formula (A):

[Chemical formula 4]

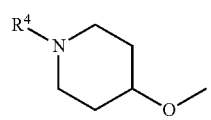

(A)

(wherein $R^4$ is $C_1$-$C_6$ alkyl (the $C_1$-$C_6$ alkyl may be substituted by one or two $C_3$-$C_7$ cycloalkyls) or $C_3$-$C_7$ cycloalkyl (the $C_3$-$C_7$ cycloalkyl may be substituted by one or two $C_1$-$C_6$ alkyls)).

In formula (A), $R^4$ is preferably $C_3$-$C_7$ cycloalkyl, and more preferably cyclobutyl.

Another preferred embodiment of the compound of formula (I) according to the present invention is where $R^1$ is $NR^{1A}R^{1B}$ (wherein $R^{1A}$ and $R^{1B}$, which may be the same or different, are each a hydrogen atom, $C_1$-$C_6$ alkyl, or $C_3$-$C_7$ cycloalkyl; alternatively, $R^{1A}$ and $R^{1B}$ are bonded together with the adjacent nitrogen atom to form a 3- to 7-membered saturated heterocyclic ring (the saturated heterocyclic ring being optionally substituted by one or two $C_1$-$C_6$ alkyls)).

Still another preferred embodiment of the compound of formula (I) according to the present invention is where $R^2$ and $R^3$ are each a hydrogen atom and n is 1.

Profiles the compounds of the present invention preferably have include high drug efficacy, superior in vivo kinetics (good oral absorption and no accumulation in particular tissues), superior properties exhibited as pharmaceuticals, low toxicity, etc. Preferred compounds of the present invention are less likely to be recognized as a substrate for P-glycoprotein which is an efflux transporter that controls intracerebral migration of drugs and hence, those compounds are expected to have superior intracerebral migration.

The "pharmaceutically acceptable salt" as used herein encompasses, for example, salts with inorganic acids such as sulfuric acid, hydrochloric acid, hydrobromic acid, phosphoric acid, and nitric acid; salts with organic acids such as acetic acid, oxalic acid, succinic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, and naphthalene-2-sulfonic acid; salts with one or more metal ions such as lithium ion, sodium ion, potassium ion, calcium ion, magnesium ion, zinc ion, and aluminum ion; and salts with ammonia or amines such as arginine, lysine, piperazine, choline, diethylamine, 4-phenylcyclohexylamine, 2-aminoethanol, and benzathine.

The compounds of the present invention may also occur in the form of various solvates. They may sometimes be in a hydrate form from the viewpoint of applicability as pharmaceuticals.

The compounds of the present invention encompass all possible forms including enantiomers, diastereomers, equilibrium compounds, mixtures thereof in any proportions, racemates, and so on. Individual isomers can be obtained by known methods, for example, use of an optically active starting material or intermediate, optically selective or diastereoselective reaction in the production of an intermediate or the final product, or chromatographic separation in the production of an intermediate or the final product.

The compounds of the present invention also encompass those in which one or more hydrogen atoms, carbon atoms, nitrogen atoms, oxygen atoms or sulfur atoms are replaced by their radioisotopes or stable isotopes. These labeled compounds are useful in, for example, studies of metabolism and pharmacokinetics, or biological analyses in which they are used as receptor ligands.

The compounds of the present invention or pharmaceutically acceptable salts thereof may be combined with one or more pharmaceutically acceptable carriers, excipients or diluents to formulate pharmaceutical preparations. Such carriers, excipients and diluents may include, for example, water, lactose, dextrose, fructose, sucrose, sorbitol, mannitol, polyethylene glycol, propylene glycol, starch, gum, gelatin, alginate, calcium silicate, calcium phosphate, cellulose, water syrup, methylcellulose, polyvinylpyrrolidone, alkyl parahydroxybenzosorbate, talc, magnesium stearate, stearic acid, glycerin, and various kinds of oil such as sesame oil, olive oil, and soybean oil.

Moreover, the above-mentioned carriers, excipients or diluents may optionally be blended with commonly used additives such as extenders, binders, disintegrants, pH modifiers, solubilizers, etc. and then processed by usual pharmaceutical formulating procedures to prepare oral or parenteral pharmaceuticals such as tablets, pills, capsules, granules, dusts, liquids/solutions, emulsions, suspensions, ointments, injections, and skin plasters. The compounds of the present invention may be given to adult patients at doses of 0.001 to 500 mg per administration, once or several times a day, by the oral or parenteral route. This dosage may be increased or decreased as appropriate for the type of disease to be treated, the age, body weight and symptom of the patient, and so on.

Pharmaceuticals containing the compounds of the present invention or pharmaceutically acceptable salts thereof as the active ingredient are useful as histamine H3 receptor antagonists or inverse agonists.

What is more, pharmaceuticals containing the compounds of the present invention or pharmaceutically acceptable salts thereof as the active ingredient are useful as preventive or therapeutic agents for dementia, Alzheimer's disease, attention-deficit hyperactivity disorder, schizophrenia, epilepsy, central convulsion, obesity, diabetes mellitus, hyperlipidemia, narcolepsy, idiopathic hypersomnia, behaviorally induced insufficient sleep syndrome, sleep apnea syndrome, circadian rhythm disorder, parasomnia, sleep related movement disorder, insomnia, depression, or allergic rhinitis.

The compounds of the present invention can be produced by known techniques in organic chemistry. Methods according to the following reaction schemes are exemplary processes for producing the compounds of the present invention and are by no means intended to limit the same. In Reaction Schemes 1 to 4 set out below, $R^1$, $R^2$, $R^3$, $R^4$, $R^5$, $R^6$, and n are as defined above. In addition, X, $Y^1$ and $Y^2$, which may be the same or different, each represent a leaving group such as a halogen atom (e.g. a chlorine atom, a bromine atom, or an iodine atom) or an organic sulfonyloxy group (e.g. a methanesulfonyloxy group, a benzenesulfonyloxy group, a p-toluenesulfonyloxy group, or a trifluoromethanesulfonyloxy group).

Described below is the process for producing a compound of the present invention that is depicted by Reaction Scheme 1. This is a process for producing the inventive compound (IA) from a compound (1).

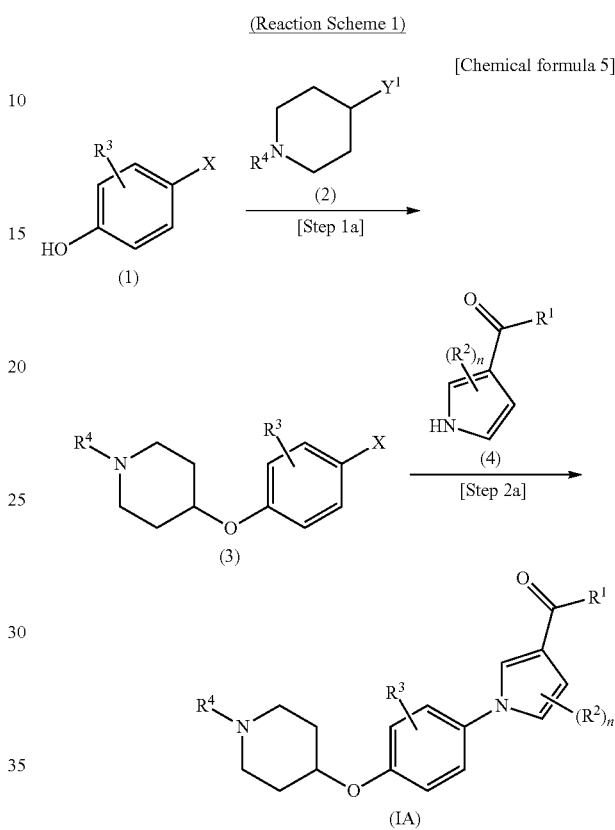

(Step 1a)

Step 1a is for achieving condensation between the compound (1) and a compound (2) by coupling reaction to form a compound (3). The compounds (1) and (2) are either known or can be readily synthesized from known compounds.

In the case where $Y^1$ is a leaving group such as a halogen atom or an organic sulfonyloxy group, the coupling reaction may be carried out by a common method involving alkylation of the hydroxyl group of phenol either in a solvent or without a solvent in the presence or absence of a base. If necessary, an additive may be added, as exemplified by potassium iodide or sodium bromide. Examples of the base that may be used in the reaction under consideration include organic bases such as pyridine, triethylamine, and diisopropylethylamine; and inorganic bases such as potassium tert-butoxide, potassium carbonate, cesium carbonate, sodium hydrogencarbonate, sodium hydroxide, potassium hydroxide, and sodium hydride. Examples of the solvent that may be used in the reaction under consideration include alcohols such as methanol, ethanol, and isopropanol; ethers such as tetrahydrofuran, 1,2-dimethoxyethane, and 1,4-dioxane; hydrocarbons such as toluene and benzene; halogenated hydrocarbons such as chloroform and dichloromethane; amides such as N,N-dimethylformamide, N,N-dimethylacetamide, and N-methyl-2-pyrrolidone; ketones such as acetone and 2-butanone; dimethyl sulfoxide; acetonitrile; water; or mixed solvents thereof. The reaction temperature for the reaction under consideration generally ranges from 0° C. to 200° C., preferably from 15° C.

to 150° C., and the reaction time generally ranges from 1 to 48 hours, preferably from 1 to 16 hours.

In the case where $Y^1$ is a hydroxyl group, the coupling reaction under consideration may be exemplified by the Mitsunobu reaction; an example of the method for carrying out this reaction is one that is performed in a solvent in the presence of a reagent comprising an organophosphorus compound such as triphenylphosphine or tributylphosphine combined with an azo compound such as diethyl azodicarboxylate, diisopropyl azodicarboxylate, or di-tert-butyl azodicarboxylate, or alternatively, in the presence of a phosphorus ylide reagent such as cyanomethylene tributyl phosphorane. Examples of the solvent that may be used in the reaction under consideration include ethers such as tetrahydrofuran, 1,2-dimethoxyethane, and 1,4-dioxane; hydrocarbons such as toluene and benzene; halogenated hydrocarbons such as chloroform and dichloromethane; amides such as N,N-dimethylformamide, N,N-dimethylacetamide, and N-methyl-2-pyrrolidone; ketones such as acetone and 2-butanone; dimethyl sulfoxide; acetonitrile; water; or mixed solvents thereof. The reaction temperature for the reaction under consideration generally ranges from 0° C. to 150° C., preferably from 15° C. to 100° C., and the reaction time generally ranges from 1 to 48 hours, preferably from 1 to 16 hours.

(Step 2a)

Step 2a is for achieving condensation between the compound (3) and a compound (4) by cross-coupling reaction to form a compound (IA) of the present invention. The compound (4) is either known or can be readily synthesized from a known compound. The cross-coupling reaction can be carried out by a common method that performs the reaction in a solvent in the presence of a catalyst and its ligand; for instance, it can be carried out according to the method described in Kunz et al., Synlett, 2003, vol. 15, pp. 2428-2439 or a modification thereof. The reaction under consideration is preferably performed in the presence of a base. Examples of the catalyst that may be used in the reaction under consideration include transition metal catalysts such as copper, nickel or palladium which are commonly used in the cross-coupling reaction, and more specifically they include copper(0), copper(I) iodide, copper(I) chloride, copper(I) oxide, copper(I) bromide triphenylphosphine complex, copper(I) trifluoromethanesulfonate benzene complex, copper(II) sulfate, palladium(II) acetate, tetrakis(triphenylphosphine)palladium (0), bis(triphenylphosphine)palladium(II) chloride, [1,1'-bis (diphenylphosphino)ferrocene]palladium(II) dichloride, tris (dibenzylideneacetone)dipalladium(0), bis(acetylacetonato) nickel(II), etc. The ligand that may be used in the reaction under consideration is selected from ligands that are commonly used in a condensation reaction that uses metal catalysts and examples include N,N'-dimethylethylenediamine, N,N'-dimethylcyclohexane-1,2-diamine, 2-aminopyridine, 1,10-phenanthroline, 3,4,7,8-tetramethyl-1,10-phenanthroline, 2-hydroxybenzaldehyde oxime, ethylene glycol, triphenylphosphine, tri-tert-butylphosphine, etc. Examples of the base that may be used in the reaction under consideration include potassium carbonate, potassium phosphate, potassium hydroxide, potassium tert-butoxide, sodium tert-butoxide, cesium carbonate, sodium carbonate, sodium hydrogencarbonate, sodium acetate, sodium methoxide, tetrabutylammonium hydroxide, etc. Examples of the solvent that may be used in the reaction under consideration include alcohols such as methanol, ethanol, and isopropanol; ethers such as tetrahydrofuran, 1,2-dimethoxyethane, and 1,4-dioxane; hydrocarbons such as toluene and benzene; halogenated hydrocarbons such as chloroform and dichloromethane; amides such as N,N-dimethylformamide, N,N-dimethylacetamide, and N-methyl-2-pyrrolidone; ketones such as acetone and 2-butanone; dimethyl sulfoxide; acetonitrile; water; or mixed solvents thereof. The reaction temperature for the reaction under consideration generally ranges from 0° C. to 200° C., preferably from 40° C. to 150° C., and the reaction time generally ranges from 1 to 48 hours, preferably from 1 to 16 hours.

Alternatively, the compound (IA) may be produced according to the method depicted by Reaction Scheme 2.

(Reaction scheme 2)

[Chemical formula 6]

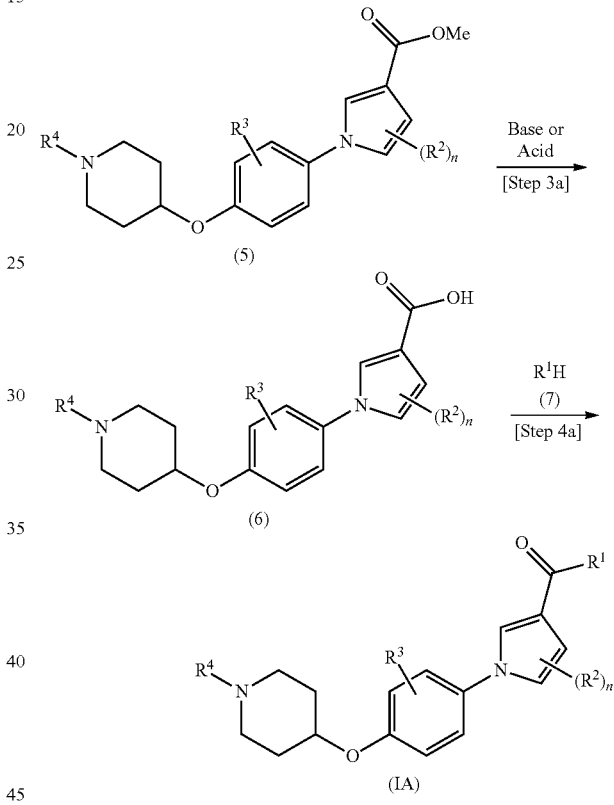

(Step 3a)

Step 3a is such that the methoxycarbonyl group of a compound (5) which is a species of the inventive compound (IA) wherein $R^1$ is a methoxy group is converted to a carboxylic acid through hydrolysis to form an inventive compound (6) in which $R^1$ is a hydroxy group. The hydrolysis reaction can be carried out by a common reaction of ester hydrolysis; for instance, it can be carried out in accordance with the methods described in T. W. Greene and P. G. M. Wuts, Protective Groups in Organic Synthesis, fourth edition, John Wiley and Sons or modifications thereof, as exemplified by a method of performing the reaction either in a solvent or without a solvent in the presence of a strong acid, and a method of performing the reaction in a solvent in the presence of a base. The reaction temperature for the reaction under consideration generally ranges from 0° C. to 120° C., preferably from 15° C. to 80° C., and the reaction time generally ranges from 1 to 48 hours, preferably from 1 to 12 hours.

(Step 4a)

Step 4a is for achieving condensation between the compound (6) and an amine derivative (7) by cross-coupling reaction to form the inventive compound (IA). The amine compound (7) is either known or can be readily synthesized from a known compound. The cross-coupling reaction can be carried out by common methods of amidating carboxylic acids, which include a method in which a carboxylic acid is converted to a carboxylic acid halide such as carboxylic acid chloride or carboxylic acid bromide and then reacted with amine, a method in which a mixed acid anhydride as obtained from a carboxylic acid and chlorocarbonic acid ester is reacted with amine, a method in which carboxylic acid is converted to an active ester such as 1-benzotriazolyl ester or succinimidyl ester and then reacted with amine, and a method in which a carboxylic acid is reacted with amine in the presence of a dehydration condensation agent. All of these reactions may be performed in a solvent in the presence or absence of a base. Examples of the dehydration condensation agent that may be used in the reaction under consideration include 3-(3-dimethylaminopropyl)-1-ethylcarbodiimide hydrochloride, dicyclohexylcarbodiimide, diphenylphosphorylazide, and carbonyldiimidazole, with an activator such as 1-hydroxybenzotriazole or hydroxysuccinimide being optionally used. Examples of the base that may be used in the reaction under consideration include pyridine, triethylamine, diisopropylethylamine, potassium carbonate, sodium carbonate, and sodium hydrogencarbonate. Examples of the solvent that may be used in the reaction under consideration include ethers such as tetrahydrofuran and 1,4-dioxane; hydrocarbons such as toluene and benzene; halogenated hydrocarbons such as chloroform and dichloromethane; amides such as N,N-dimethylformamide, N,N-dimethylacetamide, and N-methyl-2-pyrrolidone; ketones such as acetone and 2-butanone; dimethyl sulfoxide; acetonitrile; water; or mixed solvents thereof. Among them, preferred is toluene, tetrahydrofuran or N,N-dimethylformamide. The reaction temperature for the reaction under consideration generally ranges from 0° C. to 120° C., preferably from 15° C. to 40° C., and the reaction time generally ranges from 1 to 48 hours, preferably from 1 to 12 hours.

Described below is the process for producing a compound of the present invention that is depicted by Reaction Scheme 3. This is a process for producing a compound (IB) of the present invention from the compound (1).

(Reaction Scheme 3)

[Chemical formula 7]

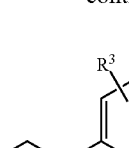

(Step 1b)

Step 1b is for obtaining a compound (9) by coupling reaction between the compound (1) and a compound (8). The compound (8) is either known or can be readily synthesized from a known compound. The coupling reaction can be carried out by the same method as in step 1a.

(Step 2b)

Step 2b is for obtaining the inventive compound (IB) by condensation between the compound (9) and the compound (4) through cross-coupling reaction. The coupling reaction can be carried out by the same method as in step 2a.

Alternatively, the compound (IB) may be produced by the method depicted by Reaction Scheme 4.

(Reaction Scheme 4)

[Chemical formula 8]

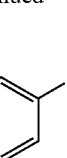

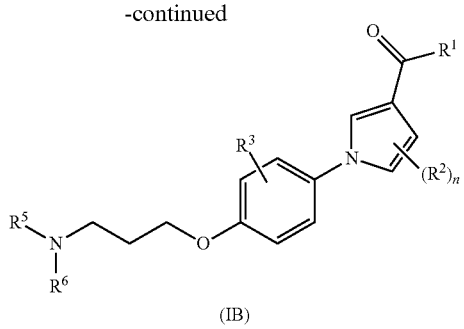

(IB)

(Step 3b)

Step 3b is such that the methoxycarbonyl group of the compound (9) which is a species of the inventive compound (IB) wherein $R^1$ is a methoxy group is converted to a carboxylic acid through hydrolysis to form an inventive compound (10) in which $R^1$ is a hydroxy group. The hydrolysis reaction can be carried out by the same method as in Step 3a.

(Step 4b)

Step 4b is for obtaining the inventive compound (IB) by condensation between the compound (10) and the amine derivative (7) through coupling reaction. The coupling reaction can be carried out by the same method as in Step 4a.

EXAMPLES

On the following pages, the present invention is described specifically by means of working examples and tests, which are not intended to limit the scope of the invention.

The instrument data listed in the working examples were obtained by measurement with the following instruments.

MS spectrum: micromass Platform LC or micromass GCT
NMR spectrum: [$^1$H-NMR] 600 MHz: JNM-ECA600 (JEOL Ltd., Japan)

Example 1

Preparation of methyl 1-{4-[(1-cyclobutylpiperidin-4-yl)oxy]phenyl}-1H-pyrrole-3-carboxylate (Compound No. 1)

[Chemical formula 9]

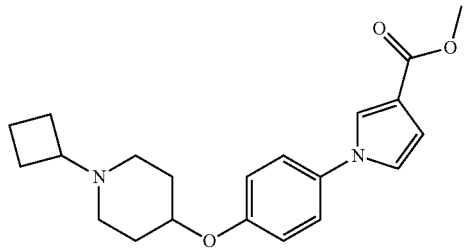

A suspension of 1-cyclobutyl-4-(4-iodophenoxy)piperidine (3 g; can be synthesized in accordance with the method described in WO2008072703), methyl 1H-pyrrole-3-carboxylic acid (1.75 g), N,N'-dimethylethylenediamine (0.592 g), copper iodide (0.32 g) and cesium carbonate (2.32 g) in toluene (8.4 mL) was stirred at 110° C. for 4 hours. The reaction mixture was left to cool to room temperature and, after adding chloroform, filtered through Celite (registered trademark). The filtrate was concentrated under reduced pressure and the resulting residue was purified by silica gel column chromatography (NH form silica gel; eluent: n-hexane/ethyl acetate=88/12-0/100) to give the titled compound as a colorless solid (1.42 g).

$^1$H NMR (600 MHz, CHLOROFORM-d) δ ppm 1.61-1.74 (m, 2H) 1.78-1.92 (m, 4H) 1.95-2.08 (m, 4H) 2.10-2.27 (m, 2H) 2.62 (br. s., 2H) 2.73 (t, J=8.05 Hz, 1H) 3.82 (s, 3H) 4.32 (br. s., 1H) 6.71 (dd, J=2.89, 1.65 Hz, 1H) 6.88-6.92 (m, 1H) 6.93-6.99 (m, 2H) 7.26-7.31 (m, 2H) 7.58 (t, J=1.86 Hz, 1H)
MS (ESI/APCI Dual) (Positive) m/z; (M+H)$^+$355

Example 2

Preparation of 1-{4-[(1-cyclobutylpiperidin-4-yl)oxy]phenyl}-1H-pyrrole-3-carboxylic acid (Compound No. 2)

[Chemical formula 10]

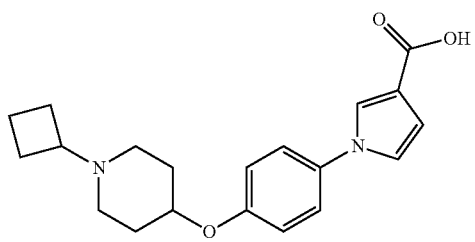

To an ethanol (8 mL) solution of methyl 1-{4-[(1-cyclobutylpiperidin-4-yl)oxy]phenyl}-1H-pyrrole-3-carboxylate (1.4 g) synthesized in Example 1, 6 N aqueous sodium hydroxide solution (1.32 mL) was added and the mixture was stirred at 60° C. for 4 hours. The reaction mixture was left to cool to room temperature and, after adding water, extracted with chloroform. The aqueous layer was neutralized with hydrochloric acid and extracted with chloroform. The combined organic layer was dried over magnesium sulfate and concentrated under reduced pressure to give the titled compound as a colorless amorphous substance (1.22 g).

$^1$H NMR (600 MHz, CHLOROFORM-d) δ ppm 1.52-3.32 (m, 15H) 4.13-4.87 (m, 1H) 6.76 (dd, J=2.89, 1.65 Hz, 1H) 6.86-7.03 (m, 3H) 7.31 (d, J=8.67 Hz, 2H) 7.58-7.68 (m, 1H)
MS (ESI/APCI Dual) (Positive) m/z; (M+H)$^+$341

Example 3

Preparation of azetidin-1-yl (1-{4-[(1-cyclobutylpiperidin-4-yl)oxy]phenyl}-1H-pyrrol-3-yl)methanone (Compound No. 3)

[Chemical formula 11]

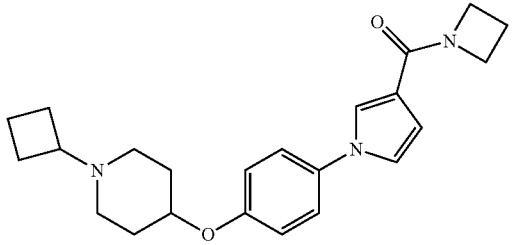

A suspension of 1-{4-[(1-cyclobutylpiperidin-4-yl)oxy]phenyl}-1H-pyrrole-3-carboxylic acid (0.1 g) synthesized in Example 2, 1-{3-(dimethylamino)propyl}-3-ethylcarbodiimide hydrochloride (0.085 g), 1-hydroxybenzotriazole hydrate (0.067 g) and aziridine (0.034 g) in N,N-dimethylformamide (0.1 ml) was stirred at room temperature for 16 hours. Water was added to the reaction mixture and extraction was conducted with chloroform. The organic layer was concentrated under reduced pressure and the resulting residue was purified by silica gel column chromatography (NH form silica gel; eluent: n-hexane/ethyl acetate=88/12-0/100) to give the titled compound as a colorless solid (0.056 g).

1H NMR (600 MHz, CHLOROFORM-d) δ ppm 1.60-1.73 (m, 2H) 1.76-1.93 (m, 4H) 1.95-2.08 (m, 4H) 2.10-2.22 (m, 2H) 2.34 (t, J=7.64 Hz, 2H) 2.54-2.68 (m, 2H) 2.70-2.82 (m, 1H) 4.11-4.23 (m, 2H) 4.28-4.35 (m, 1H) 4.37-4.55 (m, 2H) 6.53 (dd, J=2.89, 1.65 Hz, 1H) 6.83-7.00 (m, 3H) 7.25-7.33 (m, 2H) 7.44 (t, J=1.86 Hz, 1H)

MS (ESI/APCI Dual) (Positive) m/z; (M+H)$^+$380

The same procedure as described in Example 3 was repeated to give the compounds listed in the following Tables 1-1 and 1-2 (Compound Nos. 4-13).

[Chemical formula 12]

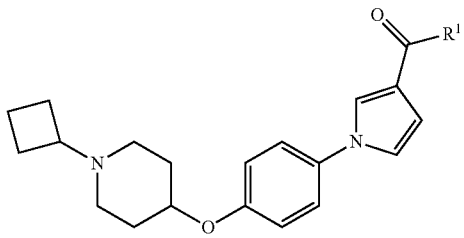

TABLE 1-1

| Compound No. | R$^1$ | Name | MS ESI/APCI observe MH$^+$ | NMR |
|---|---|---|---|---|
| 4 | pyrrolidin-1-yl | (1-{4-[(1-cyclobutylpiperidin-4-yl)oxy]phenyl}-1H-pyrrol-3-yl)(pyrrolidin-1-yl)methanol | 394 | 1H NMR (600 MHz, CHLOROFORM-d) δ ppm 1.60-1.74 (m, 2 H) 1.79-2.08 (m, 12 H) 2.08-2.27 (m, 2 H) 2.50-2.68 (m, 2 H) 2.69-2.83 (m, 1 H) 3.54-3.68 (m, 2 H) 3.69-3.85 (m, 2 H) 4.17-4.46 (m, 1 H) J = 8.67 Hz, 2 H) 7.28 (d, J = 8.67 Hz, 2 H) J = 8.67 Hz, 2 H) 7.28 (d, J = 8.67 Hz, 2 H) 7.44-7.49 (m, 1 H) |
| 5 | piperidin-1-yl | (1-{4-[(1-cyclobutylpiperidin-4-yl)oxy]phenyl}-1H-pyrrol-3-yl)(piperidin-1-yl)methanol | 408 | 1H NMR (600 MHz, CHLOROFORM-d) δ ppm 1.57-1.74 (m, 8 H) 1.78-1.94 (m, 4 H) 1.95-2.08 (m, 4 H) 2.09-2.22 (m, 2 H) 2.57-2.66 (m, 2 H) 2.69-2.81 (m, 1 H) 3.59-3.76 (m, 4 H) 4.23-4.38 (m, 1 H) 6.41 (br. s, 1 H) 6.85-6.92 (m, 1 H) 6.94 (d, J = 8.67 Hz, 2 H) 7.23-7.32 (m, 3 H) |
| 6 | N(CH$_3$)$_2$ | (1-{4-[(1-cyclobutylpiperidin-4-yl)oxy]phenyl}-N,N-dimethyl-1H-pyrrole-3-carboxamide | 368 | 1H NMR (600 MHz, CHLOROFORM-d) δ ppm 1.62-1.75 (m, 2 H) 1.78-1.94 (m, 4 H) 1.96-2.08 (m, 4 H) 2.10-2.22 (m, 2 H) 2.55-2.66 (m, 2 H) 2.68-2.81 (m, 1 H) 3.00-3.38 (m, 6 H) 4.19-4.43 (m, 1 H) 6.46-6.54 (m, 1 H) 6.86-6.91 (m, 1 H) 6.94 (d, J = 9.08 Hz, 2 H) 7.27 (d, J = 8.67 Hz, 2 H) 7.36 (br. s, 1 H) |
| 7 | NHCH$_3$ | 1-{4-[(1-cyclobutylpiperidin-4-yl)oxy]phenyl}-N-methyl-1H-pyrrole-3-carboxamide | 354 | 1H NMR (600 MHz, CHLOROFORM-d) δ ppm 1.62-1.74 (m, 2 H) 1.79-1.92 (m, 4 H) 1.96-2.07 (m, 4 H) 2.10-2.24 (m, 2 H) 2.53-2.67 (m, 2 H) 2.69-2.79 (m, 1 H) 2.96 (d, J = 4.95 Hz, 3 H) 4.19-4.38 (m, 1 H) 5.63-5.84 (m, 1 H) 6.40-6.53 (m, 1 H) 6.87-6.92 (m, 1 H) 6.95 (d, J = 9.08 Hz, 2 H) 7.23-7.31 (m, 2 H) 7.49-7.55 (m, 1 H) |
| 8 | NH$_2$ | 1-{4-[(1-cyclobutylpiperidin-4-yl)oxy]phenyl}-1H-pyrrole-3-carboxamide | 340 | 1H NMR (600 MHz, CHLOROFORM-d) δ ppm 1.62-1.74 (m, 2 H) 1.76-1.92 (m, 4 H) 1.96-2.08 (m, 4 H) 2.11-2.24 (m, 2 H) 2.55-2.67 (m, 2 H) 2.69-2.80 (m, 1 H) 4.25-4.41 (m, 1 H) 5.14-5.69 (m, 2 H) 6.51 (dd, J = 2.89, 1 65 Hz, 1 H) 6.90-6.98 (m, 3 H) 7.26-7.31 (m, 2 H) 7.55 (t, J = 2.06 Hz, 1 H) |

TABLE 1-2

| Compound No | R¹ | Name | MS ESI/APCI observe MH⁺ | NMR |
|---|---|---|---|---|
| 9 | morpholine attached via N | (1-{4-[(1-cyclobutylpiperidin-4-yl)oxy]phenyl}-1H-pyrrol-3-yl)(morpholin-4-yl)methanone | 410 | 1H NMR (600 MHz, CHLOROFORM-d) δ ppm 1.52-1.65 (m, 2 H) 1.69-1.85 (m, 4 H) 1.87-2.00 (m, 4 H) 2.03-2.15 (m, 2 H) 2.43-2.59 (m, 2 H) 2.61-2.72 (m, 1 H) 3.56-3.75 (m, 8 H) 4.15-4.31 (m, 1 H) 6.33 (dd, J = 2.89, 1.65 Hz, 1 H) 6.83 (t, J = 2.68 Hz, 1 H) 6.87 (d, J = 9.08 Hz, 2 H) 7.18-7.21 (m, 2 H) 7.25 (t, J = 2.06 Hz, 1 H) |
| 10 | 2,6-dimethylmorpholine | (1-{4-[(1-cyclobutylpiperidin-4-yl)oxy]phenyl}-1H-pyrrol-3-yl)(2R,6S)-2,6-dimethylmorpholin-4-yl)methanone | 438 | 1H NMR (600 MHz, CHLOROFORM-d) δ ppm 1.20 (d, J = 5.78 Hz, 6 H) 1.60-1.75 (m, 2 H) 1.79-1.93 (m, 4 H) 1.95-2.08 (m, 4 H) 2.10-2.24 (m, 2 H) 2.42-2.97 (m, 5 H) 3.52-3.72 (m, 2 H) 4.15-4.58 (m, 3 H) 6.34-6.46 (m, 1 H) 6.91 (d, J = 2.48 Hz, 1 H) 6.95 (d, J = 9.08 Hz, 2 H) 7.27 (d, J = 9.08 Hz, 2H) 7.32 (d, J = 1.65 Hz, 1 H) |
| 11 | 2-oxa-6-azaspiro[3.3]heptane | (1-{4-[(1-cyclobutylpiperidin-4-yl)oxy]phenyl}-1H-pyrrol-3-yl)(2-oxa-6-azaspiro[3.3]hepta-6-yl)methanone | 422 | 1H NMR (600 MHz, CHLOROFORM-d) δ ppm 1.61-1.76 (m, 2 H) 1.78-1.93 (m, 4 H) 1.96-2.08 (m, 4 H) 2.12-2.22 (m, 2 H) 2.53-2.68 (m, 2 H) 2.69-2.78 (m, 1 H) 4.18-4.67 (m, 5 H) 4.76-4.87 (m, 4 H) 6.48-6.53 (m, 1 H) 6.89-6.93 (m, 1 H) 6.95 (d, J = 9.08 Hz, 2 H) 7.27 (d, J = 8.67 Hz, 2 H) 7.40-7.45 (m, 1 H) |
| 12 | tert-butylamino | N-tert-butyl-1-{4-[(1-cyclobutylpiperidin-4-yl)oxy]phenyl}-1H-pyrrole-3-carboxamide | 396 | 1H NMR (600 MHz, CHLOROFORM-d) δ ppm 1.45 (s, 9 H) 1.60-1.76 (m, 2 H) 1.78-1.93 (m, 4 H) 1.96-2.08 (m, 4 H) 2.10-2.23 (m, 2 H) 2.50-2.67 (m, 2 H) 2.70-2.80 (m, 1 H) 4.20-4.42 (m, 1 H) 5.57-5.65 (m, 1 H) 6.38-6.44 (m, 1 H) 6.85-6.91 (m, 1 H) 6.94 (d, J = 9.08 Hz, 2 H) 7.24-7.28 (m, 2 H) 7.45-7.49 (m, 1 H) |
| 13 | cyclobutylamino | N-cyclobutyl-1-{4-[(1-cyclobutylpiperidin-4-yl)oxy]phenyl}-1H-pyrrole-3-carboxamide | 394 | 1H NMR (600 MHz, CHLOROFORM-d) δ ppm 1.59-1.77 (m, 4 H) 1.79-2.08 (m, 10 H) 2.10-2.21 (m, 2 H) 2.35-2.46 (m, 2 H) 2.51-2.66 (m, 2 H) 2.68-2.79 (m, 1 H) 4.22-4.39 (m, 1 H) 4.50-4.66 (m, 1 H) 5.78-5.92 (m, 1 H) 6.40-6.50 (m, 1 H) 6.86-6.92 (m, 1 H) 6.94 (d, J = 8.67 Hz, 2 H) 7.27 (d, J = 8.67 Hz, 2 H) 7.50 (br. s, 1 H) |

Example 4

Preparation of methyl 1-{4-[(1-cyclobutylpiperidin-4-yl)oxy]phenyl}-2,5-dimethyl-1H-pyrrol-3-carboxylate (Compound No. 14)

[Chemical formula 13]

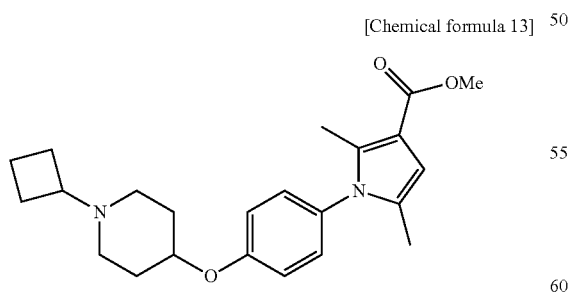

The titled compound was prepared as a colorless amorphous substance by repeating the procedure of Example 1, except that the methyl 1H-pyrrole-3-carboxylic acid was replaced by methyl 2,5-dimethyl-1H-pyrrole-3-carboxylic acid.

1H NMR (600 MHz, CHLOROFORM-d) δ ppm 1.60-1.73 (m, 2H) 1.77-1.90 (m, 4H) 1.93 (s, 3H) 1.97-2.07 (m, 4H) 2.08-2.20 (m, 2H) 2.25 (s, 3H) 2.53-2.78 (m, 3H) 3.77 (s, 3H) 4.33 (br. s., 1H) 6.30 (d, J=1.24 Hz, 1H) 6.88-6.96 (m, 2H) 7.00-7.08 (m, 2H)

MS (ESI/APCI Dual) (Positive) m/z; (M+H)⁺383

Example 5

Preparation of (1-{4-[(1-cyclobutylpiperidin-4-yl)oxy]phenyl}-2,5-dimethyl-1H-pyrrol-3-yl)(pyrrolidin-1-yl)methanone (Compound No. 15)

[Chemical formula 14]

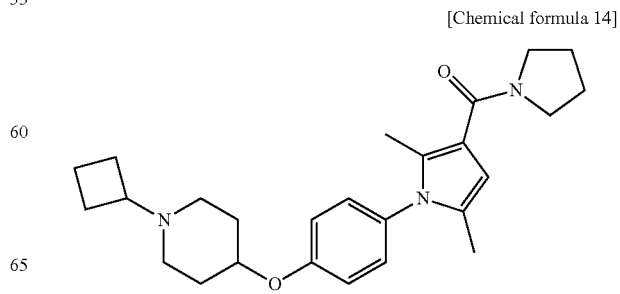

A mixture of the methyl 1-{4-[(1-cyclobutylpiperidin-4-yl)oxy]phenyl}-2,5-dimethyl-1H-pyrrole-3-carboxylate (0.06 g) synthesized in Example 4 and pyrrolidine (0.112 g) was stirred in a sealed tube at 100° C. for 16 hours. The reaction mixture was left to cool to room temperature and concentrated under reduced pressure; the resulting residue was purified by silica gel column chromatography (NH preparative silica gel plate 0.5 mm; eluent: n-hexane/ethyl acetate=50/50) to give the titled compound as a colorless solid.

1H NMR (600 MHz, CHLOROFORM-d) δ ppm 1.59-1.93 (m, 12H) 1.95 (s, 3H) 1.98-2.09 (m, 4H) 2.17 (s, 3H) 2.64 (br. s., 2H) 2.74 (t, J=8.05 Hz, 1H) 3.62 (d, J=9.91 Hz, 4H) 4.34 (br. s., 1H) 6.06 (s, 1H) 6.88-6.98 (m, 2H) 7.02-7.11 (m, 2H)

MS (ESI/APCI Dual) (Positive) m/z; (M+H)⁺422

Example 6

Preparation of [1-(4-{3-[(2R)-2-methylpyrrolidin-1-yl]propoxy}phenyl)-1H-pyrrol-3-yl](pyrrolidin-1-yl)methanone (Compound No. 16)

[Chemical formula 15]

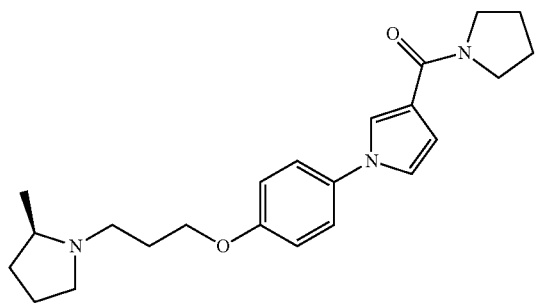

The titled compound was prepared as a colorless amorphous substance by repeating the procedure of Example 1, except that the 1-cyclobutyl-4-(4-iodophenoxy)piperidine was replaced by (2R)-1-[3-(4-iodophenoxy)propyl]-2-methylpyrrolidine (which can be synthesized in accordance with the method described in WO2009063953) and the methyl 1H-pyrrole-3-carboxylic acid by 3-(pyrrolidin-1-ylcarbonyl)-1H-pyrrole.

1H NMR (600 MHz, CHLOROFORM-d) δ ppm 1.08 (d, J=5.78 Hz, 3H) 1.35-1.48 (m, 1H) 1.63-1.83 (m, 2H) 1.85-2.04 (m, 3H) 2.11 (d, J=9.08 Hz, 1H) 2.16-2.23 (m, 1H) 2.25-2.33 (m, 1H) 2.92-2.99 (m, 1H) 3.17 (d, J=2.48 Hz, 1H) 3.65 (br. s., 4H) 3.73 (br. s., 4H) 3.96-4.15 (m, 2H) 6.63 (dd, J=3.10, 1.86 Hz, 1H) 6.89-6.97 (m, 3H) 7.27-7.32 (m, 2H) 7.45-7.49 (m, 1H)

MS (ESI/APCI Dual) (Positive) m/z; (M+H)⁺382

Example 7

Preparation of (1-{4-[(1-isopropylpiperidin-4-yl)oxy]phenyl}-1H-pyrrol-3-yl)(pyrrolidin-1-yl)methanone (Compound No. 17)

[Chemical formula 16]

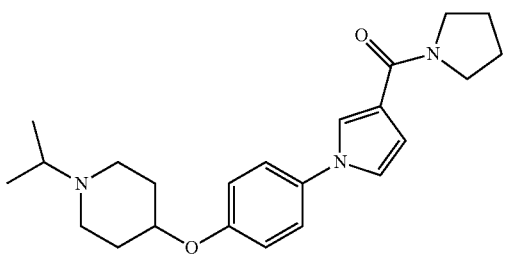

The titled compound was prepared as a colorless amorphous substance by repeating the procedure of Example 1, except that the methyl 1H-pyrrole-3-carboxylic acid was replaced by (1H-pyrrol-3-yl)(pyrrolidin-1-yl)methanone and the 1-cyclobutyl-4-(4-iodophenoxy)piperidine by 4-(4-iodophenoxy)-1-isopropylpiperidine (which can be synthesized in accordance with the method described in WO2004089373).

1H NMR (600 MHz, CHLOROFORM-d) δ ppm 1.05 (d, J=6.61 Hz, 6H) 1.74-2.07 (m, 8H) 2.39 (br. s., 2H) 2.66-2.84 (m, 3H) 3.60-3.81 (m, 4H) 4.24-4.34 (m, 1H) 6.63 (dd, J=3.10, 1.86 Hz, 1H) 6.87-7.00 (m, 3H) 7.22-7.32 (m, 2H) 7.47 (t, J=2.06 Hz, 1H)

MS (ESI/APCI Dual) (Positive) m/z; (M+H)⁺382

Example 8

Preparation of 1-{4-[(1-isopropylpiperidin-4-yl)oxy]phenyl}-N-methyl-1H-pyrrole-3-carboxamide (Compound No. 18)

[Chemical formula 17]

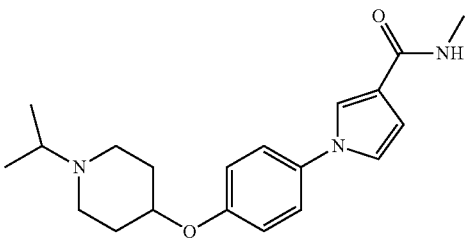

The titled compound was prepared as a colorless crystal by repeating the procedure of Example 1, except that the methyl 1H-pyrrole-3-carboxylic acid was replaced by N-methyl-1H-pyrrole-3-carboxamide and the 1-cyclobutyl-4-(4-iodophenoxy)piperidine by 4-(4-iodophenoxy)-1-isopropylpiperidine.

1H NMR (600 MHz, CHLOROFORM-d) δ ppm 1.06 (d, J=6.61 Hz, 6H) 1.82 (d, J=9.08 Hz, 2H) 1.95-2.09 (m, 2H) 2.39 (br. s., 2H) 2.79 (br. s., 3H) 2.96 (d, J=4.95 Hz, 3H)

4.19-4.39 (m, 1H) 5.59-5.86 (m, 1H) 6.45 (dd, J=2.89, 1.65 Hz, 1H) 6.84-6.99 (m, 2H) 7.17-7.32 (m, 2H) 7.52 (t, J=2.06 Hz, 1H)

MS (ESI/APCI Dual) (Positive) m/z; (M+H)$^+$342

Example 9

Preparation of (1-{4-[(1-tert-butylpiperidin-4-yl) oxy]phenyl}-1H-pyrrol-3-yl)(pyrrolidin-1-yl)methanone (Compound No. 19

[Chemical formula 18]

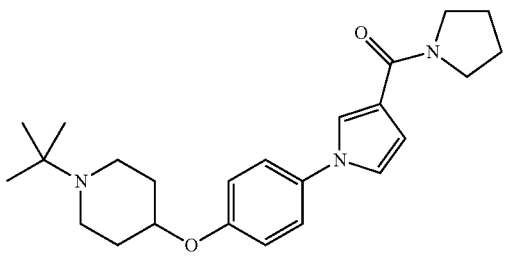

The titled compound was prepared as a colorless crystal by repeating the procedure of Example 1, except that the methyl 1H-pyrrole-3-carboxylic acid was replaced by (1H-pyrrol-3-yl)(pyrrolidin-1-yl)methanone and the 1-cyclobutyl-4-(4-iodophenoxy)piperidine by 1-tert-butyl-4-(4-iodophenoxy)piperidine (which can be synthesized in accordance with the method described in WO2008072724).

1H NMR (600 MHz, CHLOROFORM-d) δ ppm 1.09 (s, 9H) 1.81 (dd, J=8.46, 3.92 Hz, 2H) 1.86-2.06 (m, 6H) 2.41 (br. s., 2H) 2.87 (br. s., 2H) 3.56-3.80 (m, 4H) 4.22-4.32 (m, 1H) 6.63 (dd, J=3.10, 1.86 Hz, 1H) 6.85-6.99 (m, 3H) 7.23-7.31 (m, 2H) 7.41-7.50 (m, 1H)

MS (ESI/APCI Dual) (Positive) m/z; (M+H)$^+$396

Example 10

Preparation of 1-{4-[(1-tert-butylpiperidin-4-yl)oxy] phenyl}-N-methyl-1H-pyrrole-3-carboxamide (Compound No. 20)

[Chemical formula 19]

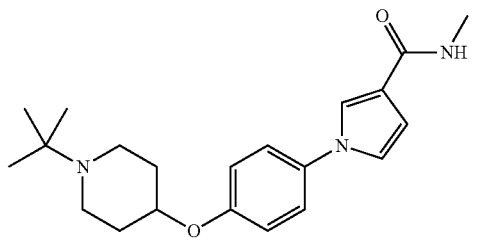

The titled compound was prepared as a colorless crystal by repeating the procedure of Example 1, except that the methyl 1H-pyrrole-3-carboxylic acid was replaced by N-methyl-1H-pyrrole-3-carboxamide and the 1-cyclobutyl-4-(4-iodophenoxy)piperidine by 1-tert-butyl-4-(4-iodophenoxy)piperidine.

1H NMR (600 MHz, CHLOROFORM-d) δ ppm 1.09 (s, 9H) 1.81 (dd, J=8.46, 3.92 Hz, 2H) 1.96-2.06 (m, 2H) 2.41 (br. s., 2H) 2.87 (br. s., 2H) 2.96 (d, J=4.95 Hz, 3H) 4.27 (br. s., 1H) 5.69-5.82 (m, 1H) 6.38-6.50 (m, 1H) 6.86-7.00 (m, 3H) 7.21-7.31 (m, 2H) 7.52 (t, J=1.86 Hz, 1H)

MS (ESI/APCI Dual) (Positive) m/z; (M+H)$^+$356

(Test 1: Rat H3 Receptor Binding Test)

The frontal cortex dissected from rats was homogenized with a Teflon homogenizer in a 50 mM Tris-HCl buffer solution (pH 7.4) containing a protease inhibitor (Complete EDTA-free; Roche Diagnostics) and 5 mM EDTA. The homogenate was centrifuged at 48,000×g for 15 minutes. The supernatant was removed and the pellet was suspended in a 50 mM Tris-HCl buffer solution (pH 7.4) containing 5 mM EDTA and centrifuged at 48,000×g for 15 minutes. The supernatant was removed and the pellet was suspended in a 50 mM Tris-HCl buffer solution (pH 7.4) containing 5 mM EDTA to give a membrane fraction. The membrane fraction (the protein content in the final reaction mixture: 75 μg), N-α-methyl[$^3$H]histamine (PerkinElmer; final concentration: 0.75 nM) and a test drug were mixed and subjected to reaction at room temperature for an hour. After the end of the reaction, the reaction mixture was suction filtered through a 96-well GF/C filter plate pretreated with 0.3% polyethyleneimine; the filters were then washed five times with a 50 mM Tris-HCl buffer solution (pH 7.4) containing 5 mM EDTA. After the washing, the filters were dried and a scintillator was added to measure the residual radioactivity on the filter with TopCount (PerkinElmer).

The residual radioactivity in the presence of 10 μM thioperamide was taken as indicative of nonspecific binding and the difference from the residual radioactivity in the absence of thioperamide was taken as indicative of specific binding. Each of the test drugs was dissolved and diluted in DMSO at varying concentrations to plot a dose-response curve from the corresponding residual radio activities; the concentration of test drug that inhibited the specific binding by 50% (IC$_{50}$) was determined from this curve. The IC$_{50}$ values of the example compounds are shown in Table 2 below.

TABLE 2

| Compound No. | IC$_{50}$ (nM) |
| --- | --- |
| 1 | 12 |
| 2 | 34 |
| 3 | 1.7 |
| 4 | 1.1 |
| 5 | 3.2 |
| 6 | 3.2 |
| 7 | 5.9 |
| 8 | 9.5 |
| 9 | 2.5 |
| 10 | 6.8 |
| 11 | 1.0 |
| 12 | 5.2 |
| 13 | 3.7 |
| 15 | 6.6 |
| 16 | 1.5 |
| 17 | 1.1 |
| 18 | 38 |
| 19 | 1.7 |
| 20 | 21 |

(Test 2: [$^{35}$S]GTP-γ-S Binding Test)

The frontal cortex dissected from rats was homogenized with a Teflon homogenizer in a 30 mM Tris-HCl buffer solution (pH 7.4) containing 2.5 mM calcium chloride dihydrate. The homogenate was centrifuged at 48,000×g for 15 minutes. The supernatant was removed and the pellet was suspended in a 30 mM Tris-HCl buffer solution (pH 7.4) containing 2.5 mM calcium chloride dihydrate and centrifuged at 48,000×g for 15 minutes. The supernatant was removed and the pellet was suspended in a 30 mM Tris-HCl buffer solution (pH 7.4) containing 2.5 mM calcium chloride dihydrate and after incubation at 37° C. for 30 minutes, the suspension was centrifuged at 48,000×g for 15 minutes. The resulting supernatant was removed and the pellet was suspended in a 20 mM HEPES buffer solution (pH 7.4) containing 100 mM sodium chloride and 10 mM magnesium chloride to give a membrane fraction. The membrane fraction (the protein content in the final reaction mixture: 20 μg), GDP (final concentration: 300 μM), adenosine deaminase (final concentration: 1 U/mL), R(−)-α-methyl histamine (final concentration: 300 nM) and a test drug were mixed and subjected to reaction at 30° C. for 20 minutes. After the end of the reaction, [$^{35}$S]GTP-γ-S (final concentration: 0.3 nM) was added and the reaction was continued for an additional 90 minutes. After the end of the reaction, the reaction mixture was suction filtered through a 96-well GF/C filter plate, which was then washed three times with a 20 mM HEPES buffer solution (pH 7.4) containing 100 mM sodium chloride and 10 mM magnesium chloride. After the washing, the filters were dried and a scintillator was added to measure the residual radioactivity on the filter with Top-Count (PerkinElmer).

The residual radioactivity in the absence of R(−)-α-methyl histamine was taken as indicative of nonspecific binding and the difference from the residual radioactivity in the presence of R(−)-α-methyl histamine was taken as indicative of specific binding. Each of the test drugs was dissolved and diluted in DMSO at varying concentrations to plot a dose-response curve from the corresponding residual radioactivities; the concentration of test drug that inhibited the specific binding by 50% ($IC_{50}$) was determined from this curve. As it turned out, Compound Nos. 3 and 7 of the present invention showed high activities, i.e., $IC_{50}$ of 100 nM or less.

(Test 3: Rat In Vivo Pharmacokinetic Study)

SD rats were given a single oral administration of Compound No. 3, 4 or 7 at a dose of 3 mg/kg and an hour after the administration, the compound's distribution among the plasma, brain, and cerebrospinal fluid was checked. Quantification was effected by a high-performance chromatography/tandem mass spectrometer API 4000 (LC-MS/MS; AB Sciex). As it turned out, Compound Nos. 3, 4 and 7 had good brain/plasma movement ratios of 4.5, 2.9 and 2.2, respectively, with the corresponding intracerebral concentrations of 78.2 ng/g, 7.06 ng/g and 408 ng/g. Both Compound Nos. 3 and 7 had a cerebrospinal fluid/plasma movement ratio of 0.3, with the corresponding cerebrospinal fluid concentrations of 5.75 ng/mL and 50.5 ng/mL, respectively.

(Test 4: P-Glycoprotein Substrate Recognition Test)

LLC-GA5-COL300 cells (Human MDR1 expressing system derived from pig kidney derived, cultured renal epithelial cell line LLC-PK1) were cultured on a transwell. Immediately before the test, the culture medium was replaced by Hank's balanced salt solution (HBSS) and the test was then conducted. A solution of an assay compound adjusted to a final concentration of 10 μM was added to the donor side of LLC-GA5-COL300 cells and after the passage of a predetermined period of time, a specified quantity of cells was sampled from the acceptor side. The concentration of the assay compound in the sample was measured by LC-MS/MS. From the amounts of the compound that accumulated and passed into the acceptor side, membrane permeation coefficients (×10$^{-6}$ cm/sec) were calculated for apical→basal and basal→apical directions and their relative ratio (efflux ratio) was determined to evaluate the P-glycoprotein substrate recognition. The efflux ratio values of Example Compounds are listed in Table 3 below.

TABLE 3

| Compound No. | Efflux ratio |
|---|---|
| 3 | 1.4 |
| 4 | 1.3 |
| 6 | 1.2 |
| 7 | 1.0 |
| 8 | 1.6 |
| 9 | 1.6 |
| 16 | 3.1 |

INDUSTRIAL APPLICABILITY

According to the present invention, there can be provided pharmaceutical products that have a potent action for inhibiting the binding to the histamine H3 receptor and which are useful in the prevention or treatment of disorders due to the histamine H3 receptor, for example, such diseases as dementia, Alzheimer's disease, attention-deficient hyperactivity disorder, schizophrenia, epilepsy, central convulsion, obesity, diabetes mellitus, hyperlipidemia, narcolepsy, idiopathic hypersomnia, behaviorally induced insufficient sleep syndrome, sleep apnea syndrome, circadian rhythm disorder, parasomnia, sleep related movement disorder, insomnia, and depression, or allergic rhinitis and this is expected to make a great contribution to the development of the pharmaceutical industry.

The invention claimed is:

1. A compound represented by formula (I)

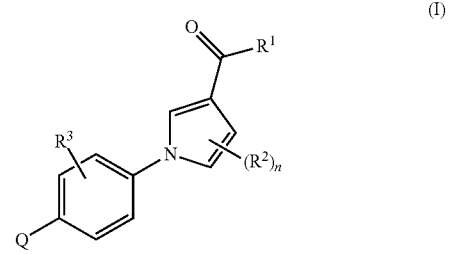

[wherein

Q refers to a group represented by the following formula (A) or (B):

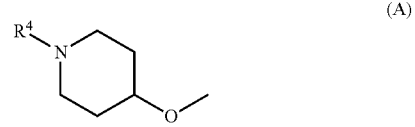

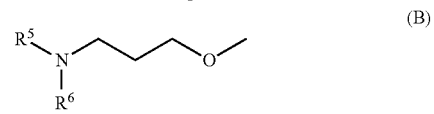

$R^1$ is hydroxyl, $C_1$-$C_6$ alkoxy, or $NR^{1A}R^{1B}$;

$R^{1A}$ and $R^{1B}$, which may be the same or different, are each a hydrogen atom, $C_1$-$C_6$ alkyl or $C_3$-$C_7$ cycloalkyl, or $R^{1A}$ and $R^{1B}$ are bonded together with the adjacent nitrogen atom to form a 3- to 7-membered saturated heterocyclic ring (the saturated heterocyclic ring being optionally substituted by one or two $C_1$-$C_6$ alkyls);

$R^2$ is a hydrogen atom, a halogen atom, or $C_1$-$C_6$ alkyl;

n is 1 or 2;

$R^3$ is a hydrogen atom, a halogen atom, or $C_1$-$C_6$ alkyl;

$R^4$ is $C_1$-$C_6$ alkyl (the $C_1$-$C_6$ alkyl may be substituted by one or two $C_3$-$C_7$ cycloalkyls) or $C_3$-$C_7$ cycloalkyl (the $C_3$-$C_7$ cycloalkyl may be substituted by one or two $C_1$-$C_6$ alkyls);

$R^5$ and $R^6$, which may be the same or different, are each $C_1$-$C_6$ alkyl or $C_3$-$C_7$ cycloalkyl, or $R^5$ and $R^6$ are bonded together with the adjacent nitrogen atom to form a 3- to 7-membered saturated heterocyclic ring (the saturated heterocyclic ring being optionally substituted by one or two $C_1$-$C_6$ alkyls)] or a pharmaceutically acceptable salt thereof.

2. A compound according to claim 1, wherein Q is represented by formula (A):

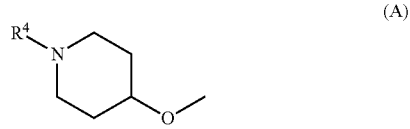

(wherein $R^4$ is as defined in claim 1), or a pharmaceutically acceptable salt thereof.

3. A compound according to claim 1, wherein $R^1$ is $NR^{1A}R^{1B}$ (wherein $R^{1A}$ and $R^{1B}$ are as defined in claim 1, or a pharmaceutically acceptable salt thereof.

4. A compound according to claim 1, wherein $R^2$ and $R^3$ are each a hydrogen atom and n is 1, or a pharmaceutically acceptable salt thereof.

5. A compound according to claim 1, wherein $R^4$ is $C_3$-$C_7$ cycloalkyl, or a pharmaceutically acceptable salt thereof.

6. A pharmaceutical composition comprising as the active ingredient a compound according to claim 1, or a pharmaceutically acceptable salt thereof and a pharmaceutically acceptable carrier, excipient or diluent.

7. A compound according to claim 1 which is selected from the group consisting of the following or a pharmaceutically acceptable salt thereof:

Methyl 1-{4-[(1-cyclobutylpiperidin-4-yl)oxy]phenyl}-1H-pyrrole-3-carboxylate,
1-{4-[(1-cyclobutylpiperidin-4-yl)oxy]phenyl}-1H-pyrrole-3-carboxylic acid,
Azetidin-1-yl(1-{4-[(1-cyclobutylpiperidin-4-yl)oxy] phenyl}-1H-pyrrol-3-yl) methanone,
(1-{4-[(1-cyclobutylpiperidin-4-yl)oxy]phenyl}-1H-pyrrol-3-yl)(pyrrolidin-1-yl) methanol,
(1-{4-[(1-cyclobutylpiperidin-4-yl)oxy]phenyl}-1H-pyrrol-3-yl)(piperidin-1-yl) methanol,
(1-{4-[(1-cyclobutylpiperidin-4-yl)oxy]phenyl}-N,N-dimethyl-1H-pyrrole-3-carboxamide,
1-{4-[(1-cyclobutylpiperidin-4-yl)oxy]phenyl}-N-methyl-1H-pyrrole-3-carboxamide,
1-{4-[(1-cyclobutylpiperidin-4-yl)oxy]phenyl}-1H-pyrrole-3-carboxamide,
(1-{4-[(1-cyclobutylpiperidin-4-yl)oxy]phenyl}-1H-pyrrol-3-yl)(morpholin-4-yl) methanone,
(1-{4-[(1-cyclobutylpiperidin-4-yl)oxy]phenyl}-1H-pyrrol-3-yl)((2R,6S)-2,6-dimethylmorpholin-4-yl)methanone,
(1-{4-[(1-cyclobutylpiperidin-4-yl)oxy]phenyl}-1H-pyrrol-3-yl)(2-oxa-6-azaspiro[3.3]hepta-6-yl)methanone,
N-tert-butyl-1-{4-[(1-cyclobutylpiperidin-4-yl)oxy]phenyl}-1H-pyrrole-3-carboxamide,
N-cyclobutyl-1-{4-[(1-cyclobutylpiperidin-4-yl)oxy]phenyl}-1H-pyrrole-3-carboxamide,
Methyl 1-{4-[(1-cyclobutylpiperidin-4-yl)oxy]phenyl}-2,5-dimethyl-1H-pyrrole-3-carboxylate,
(1-{4-[(1-cyclobutylpiperidin-4-yl)oxy]phenyl}-2,5-dimethyl-1H-pyrrol-3-yl) (pyrrolidin-1-yl)methanone,
[1-(4-{3-[(2R)-2-methylpyrrolidin-1-yl] propoxy}phenyl)-1H-pyrrol-3-yl](pyrrolidin-1-yl) methanone,
(1-{4-[(1-isopropylpiperidin-4-yl)oxy]phenyl}-1H-pyrrol-3-yl)(pyrrolidin-1-yl) methanone,
1-{4-[(1-isopropylpiperidin-4-yl)oxy]phenyl}-N-methyl-1H-pyrrole-3-carboxamide,
(1-{4-[(1-tert-butylpiperidin-4-yl)oxy]phenyl}-1H-pyrrol-3-yl)(pyrrolidin-1-yl) methanone, and
1-{4-[(1-tert-butylpiperidin-4-yl)oxy]phenyl}-N-methyl-1H-pyrrole-3-carboxamide.

8. A compound according to claim 1 which is 1-{4-[(1-cyclobutylpiperidin-4-yl)oxy]phenyl}-N-methyl-1H-pyrrole-3-carboxamide represented by the following formula or a pharmaceutically acceptable salt thereof

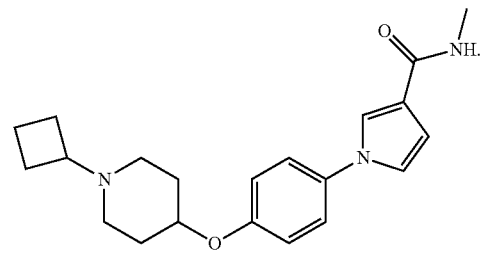 [SMILES: CNC(=O)c1ccn(-c2ccc(OC3CCN(C4CCC4)CC3)cc2)c1]

* * * * *